United States Patent [19]

Wilson

[11] Patent Number: 4,959,380
[45] Date of Patent: Sep. 25, 1990

[54] METHOD OF TREATING PEOPLE TO STOP SMOKING AND COMPOSITION

[76] Inventor: Jordan E. Wilson, 967 Continental, Detroit, Mich. 48215

[21] Appl. No.: 286,183

[22] Filed: Dec. 19, 1988

[51] Int. Cl.$^5$ .................... A61K 31/44; A61K 31/125
[52] U.S. Cl. .................................. 514/356; 514/692; 514/813
[58] Field of Search ........................ 514/356, 813, 692

*Primary Examiner*—Stanley J. Friedman
*Attorney, Agent, or Firm*—Dykema Gossett

[57] ABSTRACT

A method of treating people to stop smoking comprising the steps of brewing strong tea in an open container, partly immersing a plurality of cigarettes into the tea for 4 to 8 hours until the tea is absorbed into the cigarettes throughout their length and staining the cigarettes to a dark brown color, placing the container in an enclosed room in an atmosphere of vaporized camphor crystals for a limited period, breathing the camphorized atmosphere while visually concentrating upon the appearance of the cigarettes in the container and smelling the exuded nicotine and caffeine aroma from the container for a period of about 20 minutes, and psychologically reacting to the appearance of the cigarettes and the aroma of the caffeine and nicotine in a lung-cleansing camphor atmosphere, the user losing all interest in smoking another cigarette. A composition comprises a strong brewed aqueous solution of tea in a closed container, a concentrate of nicotine mixed in the solution, and a quantity of crystallized camphor dissolved into the solution. This solution provides a dark brown colored homogeneous mixture in solution, the fumes rising from the solution when exposed to atmosphere adapted to be inhaled for producing a psychological reaction to the appearance of the solution, the aroma of caffeine and nicotine relative to the lung-cleansing camphor atmosphere whereby the user loses all interest in smoking.

13 Claims, No Drawings

METHOD OF TREATING PEOPLE TO STOP SMOKING AND COMPOSITION

FIELD OF INVENTION

The present invention relates to smoking and more particularly, a method of treating people to stop smoking and a composition.

BACKGROUND OF THE INVENTION

The smoking habit for so many smokers is so intense and in many cases so addictive that the smoker finds it almost impossible to stop smoking. Various efforts have been made by smokers to discontinue smoking, such as a cold turkey interruption, which for many does not work effectively. Chewing beeswax, pine rosin, eating candy, and peppermints have been tried. Mint tipping of cigarettes has not been effective. The addition of chemicals designed to sicken the user or otherwise render smoking obnoxious to the user have not produced good results. Previously, many smokers have interrupted smoking by sheer will power for a limited period. Some have been successful, and many more have not been successful and have started smoking again.

SUMMARY OF THE INVENTION

An important feature of the present invention is a novel method of treating people to stop smoking wherein, to the extent known and tried by the inventor, the use of the present method has resulted in the inventor completely giving up smoking after 51 years of continuous smoking. The inventor has not smoked since his single treatment in accordance with the present method.

An important feature of the present invention is the use of a composition which includes a strong tea brewed in a container and, partly immersing a quantity of cigarettes in the tea for a period of 4 to 8 hours until the tea is absorbed into the cigarettes throughout their length. This results in staining the cigarettes to a dark brown color. A further step includes placing the container in an enclosed room in an atmosphere of vaporized camphor crystals for a limited period and thereafter breathing the camphorized atmosphere while visually concentrating upon the appearance of the cigarettes in the vessel, smelling the exuded nicotine and caffeine aroma from the container for a period of about 20 minutes and psychologically reacting to the appearance of the cigarettes and the aroma of the caffeine and nicotine in an imagined lung-cleansing camphor atmosphere, the user losing all interest in smoking another cigarette.

An important feature includes the step after brewing the tea of immersing a plurality of absorbent cotton balls into the tea.

As another feature, the step of immersing a plurality of cigarettes into the tea includes six to eight cigarettes.

Another feature includes placing the container in an enclosed room in an atmosphere of camphorized crystals for a limited period of 5 to 10 minutes approximately.

As still another feature, after the step of breathing the camphorized atmosphere for the initial period of 20 minutes, there is the further step of leaving the camphor vapor room for about 5 minutes and returning for 8 to 15 minutes more and repeating the breathing of the camphorized atmosphere while visually concentrating upon the appearance of the cigarettes in the tea solution.

As still another feature, the present method includes the further step of psychologically and imaginatively experiencing the disintegration and cleansing of the tar and nicotine lining the user's lungs.

As another feature, there is provided a composition which includes a strong brewed aqueous solution of tea in a closed container with a concentrate of nicotine mixed into the solution and a quantity of crystallized camphor dissolved into the solution to provide a dark brown, homogenous mixture in solution.

As another feature, the fumes rising from the solution when exposed to atmosphere are adapted to be inhaled for producing a psychological reaction to the appearance of the solution, the aroma of caffeine and nicotine relative to the imagined lung-cleansing camphor atmosphere whereby the user loses all interest in smoking.

These and other features and objects will be seen from the following specification and claims.

DETAILED DESCRIPTION OF AN EMBODIMENT OF THE INVENTION

The present method of treating people to stop smoking comprises the initial step of brewing strong tea in an open container. The container in the illlustrative embodiment is a saucer, two inches deep and five inches in diameter. Two teabags are used with one-half cup of boiling water, and the tea is brewed until it is strongly brewed to produce a dark brown cloring. Any caffeine-based tea may be used.

A further step includes immersing a plurality of absorbent cotton balls into the tea until the cotton balls have absorbed a portion of the liquid tea within the container.

In the illustrative embodiment, 20 cotton balls are preferred. However, it is contemplated that 10 to 20 cotton balls could be used.

A further step includes partly immersing a plurality of cigarettes such as 6 to 8 cigarettes into the tea and cotton balls for 4 to 8 hours approximately until the tea is absorbed into the cigarettes throughout their length, staining the cigarettes to a dark brown color.

A further step includes placing the container in an enclosed room in an atmosphere of vaporized camphor crystals for a limited period.

In the preferred embodiment, the enclosed room has a floor dimension of 7 by 9 feet approximately. In producing an atmosphere of the vaporized camphor crystals, there is provided within the room a rug or carpet approximately 2½ by 5 feet in dimension and dispersing over its surface 1¾ cups approximately, of a crystallized camphor.

In the illustrative embodiment, the crystallized camphor on the carpet is left in the room with the room closed for about 5 minutes. 5 to 10 minutes should be sufficient to vaporize the room and to provide a camphor vapor in the room atmosphere.

According to the dictionary definition of camphor, it is a tough, gummy, volatile, fragrant, crystalline compound. It has the formula $C_{10}H_{10}O$ and is taken from the wood or bark of a camphor tree. It is used as a carminative and stimulant in medicine. It is also used as an insect repellent. It is the characteristic of volatility of the camphor and characteristic odor which provides within a limited period a camphorized atmosphere for the enclosed room within which the container with the tea, cotton balls and cigarettes have been placed.

A further step includes the user entering the enclosed room with the camphorized atmosphere and sitting on a bed or chair, breathing the camphorized atmosphere while visually concentrating upon the appearance of the cigarettes in the container and smelling the exuded nicotine and caffeine aroma from the container over a period of about 20 minutes.

During the previous step, the user is psychologically reacting to the appearance of the cigarettes which are colored and stained a dark brown and the aroma of the caffeine and nicotine in an imagined lung-cleansing camphor atmosphere. The user thereafter loses all interest in smoking another cigarette.

After the initial twenty-minute treating step, there is the further step of leaving the camphor vapor room for about 5 minutes and returning for 8 to 15 minutes more and repeating the breathing step, at the same time concentrating upon the appearance of the cigarettes in the container and smelling the exuded nicotine and caffeine aroma from the container.

Further in accordance with the present method of psychologically reacting to the appearance of the cigarettes, the user psychologically and imaginatively experiences disintegration and cleansing of tar and nicotine from the lining of his lungs.

It is contemplated that the step of using the absorbent cotton balls could be omitted and wherein the cigarettes are partly immersed within the strong brewed tea for 4 to 8 hours approximately, until the tea is absorbed into the cigarettes throughout their length, thereby staining the tea to a dark brown color.

After the second 8 to 15 minute interval of breathing within the camphorized atmosphere of the closed room, the door is opened to let the camphorized atmosphere expand throughout the house until its presence in the room is neglible.

The foregoing method steps can be repeated once or twice thereafter on different days, if the first use of the present method seems insufficient for accomplishing the purpose of the user losing interest in smoking cigarettes.

THE COMPOSITION

It is contemplated as part of the present invention that a composition may be marketed which achieves results similar to those obtained by use of the present method and wherein a strong brewed aqueous solution of tea is stored within a closed container.

The composition further includes a concentrate of nicotine mixed into the solution, and thereafter a quantity of crystallized camphor is dissolved into the solution, thereby providing a dark brown-colored homogeneous mixture in solution. The fumes rising from the solution when exposed to atmosphere are adapted to be inhaled for producing a psychological reaction to the appearance of the solution as dark-inhaled for producing a psychological reaction to the appearance of the solution as darkbrown, simulating the color tar and nicotine known to coat the lungs of smokers.

Similar psycological reactions of the user are obtained. Inhalation of the vapors should containue for about 5 to 20 minutes, and if needed repeated on subsequent days. As an example of the foregoing composition, the ingredients are as follows.

| tea solution | 4 ounces |
| nicotine | 5/10 ounce |
| crystallized camphor | 5/10 ounce |

The composition further comprises the foregoing ingredients in the following proportions by weight:

| tea solution | 80% |
| nicotine | 10% |
| crystallized camphor | 10% |

The foregoing composition also comprises said ingredients in the following proportions by weight approximately

| tea solution | 70-90% |
| nicotine | 5 to 15% |
| crystallized camphor | 5 to 15% |

While in the preferred embodiment cyrstallized camphor is used, since it is more easily vaporized in an enclosed room, mothballs could be employed for this purpose when spread over the surface of a rug or carpet.

Another objective of the present invention is to try to combat cancer and other smoking disorders. The present method and composition is believed to be beneficial for people discontinuing usage of tobacco in all other forms such as in pipes, cigars, chewing tobacco of all descriptions and snuffs. The present method may also be helpful in conbatting the habitual abuse of marijuana and other drugs. Having described my invention, reference should now be had to the following claims.

I claim:

1. The method of treating people to stop smoking comprising the steps of:
    (a) brewing strong caffeine-based tea in an open container including about two tea bags and one-half cup of boiling water;
    (b) immersing 10 to 20 absorbent cotton balls in the tea;
    (c) partly immersing 6 to 8 cigarettes into the tea and cotton balls for 4 to 8 hours until the tea is absorbed into the cigarettes throughout their length and staining the cigarettes to a dark brown color;
    (d) dispersing about 1¾ cups of cyrstallized camphor in an enclosed room:
    (e) placing the container in said enclosed room in an atmosphere of vaporized camphor crystals for 5 to 10 minutes; and
    (f) breathing the camphorized atmosphere while visually concentrating upon the appearance of the cigarettes in the container and smelling the exuded nicotine and caffeine aroma from the container for a period of about 20 minutes;
    some users psychologically responding to the appearance of the cigarettes and the aroma of the caffeine and nicotine in a lung-cleansing camphor atmosphere and losing all interest in smoking another cigarette.

2. In the method of treating people to stop smoking of claim 1, further comprising in step a, the container being a saucer having a dimension two inches deep and five inches wide approximately.

3. In the method of treating people to stop smoking of claim 1, further comprising in step e, leaving the camphor vapor room for about five minutes and returning for eight to fifteen minutes more and repeating step e.

4. In the method of treating people to stop smoking of claim 1, further comprising in step e, said atmosphere including a piece of carpeting with the camphor crystals dispersed over its top surface.

5. In the method of treating people to stop smoking of claim 4, the carpet having a dimension of 2½ by five feet, approximately.

6. In the method of treating people to stop smoking of claim 1, some users psychologically and imaginatively experiencing disintegration and cleansing of the user's tar and nicotine lining of the user' lungs.

7. In the method of treating people to stop smoking of claim 1, further comprising in step d, the room having a floor dimension of about 7×9 feet.

8. The method of treating people to stop smoking comprising the steps of:
  (a) brewing strong caffeine-based tea in an open container including about two tea bags and one-half cup of boiling water;
  (b) partly immersing 6 to 8 cigarettes in the tea for 4 to 8 hours until the tea is absorbed into the cigarettes throughout their length and staining the cigarettes to a dark brown color;
  (c) dispersing about 1¾ cups of crystallized camphor in an enclosed room;
  (d) placing the container in said enclosed room in an atmosphere of vaporized camphor crystals for 5 to 10 minutes; and
  (e) breathing the camphorized atmosphere while visually concentrating upon the appearance of the cigarettes in the container and smelling the exuded nicotine and caffeine aroma from the container for a period of about 20 minutes;
  some users psychologically responding to the appearance of the cigarettes and the aroma of the caffeine and nicotine in a lung-cleansing camphor atmosphere and losing all interest in smoking another cigarette.

9. In the composition comprising:
  a strong aqueous solution of tea brewed in a container;
  a concentrate of nicotine mixed into the solution; and
  a quantity of crystallized camphor dissolved into the solution providing a dark brown colored homogeneous mixture in solution;
  fumes rising from the solution when exposed to atmosphere adapted to be inhaled for producing a psychological reaction to the appearance of the solution, the aroma of caffeine and nicotine relative to the lung-cleansing camphor atmosphere whereby the user looses all interest in smoking.

10. In the composition of claim 9, further comprising the foregoing ingredients and the following amounts:
  tea solution 4 oz.;
  nicotine 0.5 oz.;
  crystallized camphor 0.5 oz.

11. In the composition of claim 9, further comprising the foregoing ingredients and the following proportions by weight:
  tea solution 80 percent;
  nicotine 10 percent;
  crystallized camphor 10 percent.

12. In the composition of claim 9, further comprising the foregoing ingredients and the following proportions by weight:
  tea solution 70 to 90 percent;
  nicotine 5 to 15 percent;
  cyrstallized camphor 5 to 15 percent.

13. In the composition of claim 9, further comprising, the user imaginatively experiencing disintegration and cleansing of tar and nicotine from the lining of the user's lungs.

* * * * *